United States Patent
Donate et al.

(10) Patent No.: US 8,883,472 B2
(45) Date of Patent: *Nov. 11, 2014

(54) PROCESS FOR REMOVING WATER FROM AQUEOUS SOLUTIONS OF PROTEINS

(75) Inventors: Felipe A. Donate, Midland, MI (US); Timothy C. Frank, Midland, MI (US); Barbara J. Grabowski, Midway Park, NC (US)

(73) Assignee: Dow AgroSciences, LLC., Indianapolis, IN (US)

( * ) Notice: Subject to any disclaimer, the term of this patent is extended or adjusted under 35 U.S.C. 154(b) by 1116 days.

This patent is subject to a terminal disclaimer.

(21) Appl. No.: 10/590,095

(22) PCT Filed: Feb. 18, 2005

(86) PCT No.: PCT/US2005/005150
§ 371 (c)(1),
(2), (4) Date: May 10, 2007

(87) PCT Pub. No.: WO2005/092915
PCT Pub. Date: Jun. 10, 2005

(65) Prior Publication Data
US 2008/0021204 A1 Jan. 24, 2008

Related U.S. Application Data

(60) Provisional application No. 60/548,405, filed on Feb. 27, 2004.

(51) Int. Cl.
C07K 1/00 (2006.01)
C07K 1/14 (2006.01)

(52) U.S. Cl.
CPC ........................... *C07K 1/145* (2013.01)
USPC .......................................... 435/183; 530/421

(58) Field of Classification Search
USPC ...................................................... 530/421
See application file for complete search history.

(56) References Cited

U.S. PATENT DOCUMENTS

| | | | |
|---|---|---|---|
| 3,556,739 A * | 1/1971 | Baniel et al. | 423/321.1 |
| 4,233,210 A * | 11/1980 | Koch | 530/379 |
| 4,275,234 A * | 6/1981 | Baniel et al. | 562/584 |
| 4,642,288 A | 2/1987 | Elia De Miguel et al. | |
| 5,628,906 A * | 5/1997 | Shinnar et al. | 210/634 |
| 6,638,749 B1 | 10/2003 | Beckman et al. | |
| 2007/0193960 A1 | 8/2007 | Frank | |
| 2009/0023902 A1 | 1/2009 | Frank | |

FOREIGN PATENT DOCUMENTS

WO    WO 01/47947 A    5/2001

OTHER PUBLICATIONS

Raghavarao et al., Aqueous two phase extraction-an environmentally benign technique, Clean Technology Environmetal Policy, vol. 5, 2003, p. 136-141.*
Ullmann et al., Phase Transition extraction using solvent mixtures with critical point of miscibility, AIChE Journal, vol. 41, 1995, p. 488-500.*
Persson et al., Purification of recombinant proteins using thermoseparating aqueous two-phase system and polymer recycling, Journal of Chemical Technology and Biotechnology, vol. 74, 1999, p. 238-243.*
Davison et al., Mutual solubility of water and glycerol and glycol ethers, Journal of Chemical and Engineering Data, vol. 11, 1966, p. 404-406.*
Stephenson, Mutual solubilites: water-glycol ethers and water-glycol esters, Journal of Chemical Engineering Data, vol. 38, 1993, p. 134-138.*
Allen et al., Use of Glycol ethers for selective release of Periplasmic proteins from gram-negative bacteria, Biotechnology Progess, 2007, vol. 23, p. 1163-1170.*
Sivars U et al: "Protein partitioning in weakly charged polymer-furfactant aqueous two-phase systems" Journal of Chromatography B: Biomedical Applications, Elsevier . Science Publishers NL, vol. 680, No. 1, May 17, 1996, pp. 43-53, XP004044012, ISSN: 0378-4347 the entire document, particularly p. 46, tables 2, 3, and 6, chapter 3 Results.
SU 874 089 A1 (UK NI Uglekhimicheskij Institute) Oct. 23, 1981 cited in the application the whole document.
PCT Preliminary Report on Patentability for International Application No. PCT/US2005/005150, Mailed Sep. 8, 2006, from the International Bureau of W.I.P.O. Authorized Officer: Philippe Becamel.

* cited by examiner

*Primary Examiner* — Jon P Weber
*Assistant Examiner* — Tiffany Gough
(74) *Attorney, Agent, or Firm* — Ronald S. Maciak; TraskBritt, P.C.

(57) ABSTRACT

A method for extracting water from an aqueous solution of a protein comprising the steps of:
(a) intermixing the aqueous solution of the protein with a sufficient quantity of at least one glycol ether at a temperature at least 30 centigrade degrees above the lower critical solution temperature (LCST), preferably at least 20 centigrade degrees above the LCST, and most preferably at least 10 degrees above the LCST, to form a suspension comprising a concentrated aqueous protein phase and a liquid organic phase comprising said at least one glycol ether and at least 10 percent water extracted from the aqueous solution of the protein, wherein the glycol ether has an inverse solubility in water, with the proviso that the solubility of the glycol ether in water is significantly less than the solubility of water in the glycol ether, and the glycol ether does not significantly deactivate the protein, and
(b) separating the concentrated aqueous protein phase formed in step (a) from at least a portion of the liquid organic phase.

15 Claims, No Drawings

PROCESS FOR REMOVING WATER FROM AQUEOUS SOLUTIONS OF PROTEINS

This application claims the benefit of U.S. Provisional Patent Application Ser. No. 60/548,405, filed Feb. 27, 2004.

The present invention relates to a process for removing water from aqueous solutions of proteins including enzymes and therapeutic proteins by liquid-liquid extraction.

Enzymes are highly efficient protein catalysts which are involved in almost every biological reaction. The enzymes are grouped in into six major classes on the basis of the type of reaction catalyzed, that is, Oxidoreductase, Transferase, Hydrolase, Lyase, Isomerase and Ligase. Enzymes find use in chemical analysis, clinical diagnosis and a broad range of industrial applications. Enzymes may be extracted from any living organism but most are obtained by the fermentation of micro-organisms. Industrial preparation of industrial enzymes aims for economy, effectiveness and safety.

Therapeutic proteins are proteins with specific biological activity that make them effective as pharmaceutical agents or drugs for treatment of disease, or as adjuncts to therapy used in combination with a drug or mixture of drugs. In certain cases, therapeutic proteins may be produced via bacterial fermentation using the methods of genetic engineering to cause the host microbe to produce a specific protein or mixture of proteins having the desired activity. Often, these recombinant proteins are produced within the cell of the organism and must be recovered from the cell after harvesting the broth. Because therapeutic proteins are used as drugs or in combination with drugs, the purity of the isolated protein or protein mixture is a critical factor in their manufacture. This is especially important for proteins that must be injected into the bloodstream to effectively treat disease.

Various methods for concentration of aqueous solutions of proteins are well known and described in the literature. These methods include ultrafiltration, various forms of chromatography and ion exchange, evaporation of water, as well as aqueous two-phase extraction (also called aqueous biphasic partitioning) using water-soluble polymers (including polyglycols and nonionic surfactants). See, for example, M. P. Deutscher, Ed., "Guide to Protein Purification," Methods in Enzymology," Vol. 182, Academic Press, San Diego (1990); H. B. Blanch and D. S. Clark, "Biochemical Engineering," Marcel Dekker, New York, 1997, pp. 474-482; P. A. Belter, E. L. Cussler and W. Hu, "Bioseparations: Downstream Processing for Biotechnology," Wiley, New York, 1988, Chapter 5, pp. 99-143; and M. R. Ladisch, "Bioseparation Engineering," Wiley Interscience, New York, 2001.

Aqueous two-phase extraction has been widely used for the separation and concentration of proteins and nucleic acids. The two-phase aqueous systems are generally made up of (i) two immiscible polymer components, both water-soluble, such as polyethylene glycol and dextran; or (i) a single polymer component, such as polyethylene glycol, and aqueous salt solution; or (iii) water-miscible organic solvent, such as ethanol, and aqueous salt solution; or (iv) a non-ionic detergent and hydrophilic polymers, such as polyethylene glycol and dextran. See, for example, A. Louwrier, "Model Phase Separations of Proteins Using Aqueous/Ethanol Components", Biotechnology Techniques, Vol. 12, No. 6, pp. 363-365 (1998); A. Louwrier, "Model Isolations of Nucleic Acids from Prokaryotic Sources Using an Inorganic/Aqueous Biphasic System", Biotechnology Techniques, 13, pp. 329-330 (1999); A. Louwrier, "Nucleic Acid Removal from Taq Polymerase Preparations Using an Aqueous/Organic Biphasic System", Biotechnology Techniques, 27, pp. 444-445 (1999); Ulf Sivars et al, "Mechanism of Phase Behavior and Protein Partitioning in Detergent/Polymer Aqueous Two-Phase Systems for Purification of Integral Membrane Proteins", Biochemica and Biophysica Acta, 1474, pp. 133-146 (2000); and Jorge Lorwin et al, "Oxidative Renaturation of Hen Egg-White Lysosyme in Polyethylene-Salt Aqueous Two-Phase Systems", Biotechnology and Bioengineering, Vol. 65, No. 4, pp. 437-446 (1999), Methods for concentrating proteins contained in aqueous solution should not result in significant deactivation of the desired protein, or it becomes necessary to add additional processing steps for reactivation. These reactivation steps can include methods for refolding the desired protein to obtain the required structure of the active form of the protein. Often, in these refolding steps, it is not possible to reactivate all of the protein and only a fraction can be recovered in the active form.

Also, many valuable hydrophilic organic compounds such as carboxylic acids, sulfonic acids, polyhydroxy compounds, amino acids and amides are produced via fermentation or other manufacturing processes involving aqueous streams. Various methods, such as, for example, steam stripping, liquid-liquid extraction, liquid solid adsorption, chromatography and membrane-based methods, are known for the recovery and concentration of these valuable hydrophilic compounds from aqueous liquor containing same such as, for example, fermentation broths and waste water streams. Typically, in a liquid-liquid extraction process, an oxygenated solvent having limited solubility in water is employed. The hydrophilic organic compound is than recovered from the oxygenated solvent phase and concentrated by various known recovery methods. See, for example, U.S. Pat. No. 5,426,219 (W. Lenhardt et al.), U.S. Pat. No. 3,556,739 (A. Baniel et al.), U.S. Pat. No. 4,322,550 (J. Kimble), U.S. Pat. No. 5,628,906 (R. Shinnar et al.), U.S. Pat. No. 4,954,260 (Z. Ludmer et al.), U.S. Pat. No. 6,229,046 B1 (A. Eyal et al.) and U.S. Pat. No. 6,320,077 B1 (A. Eyal et al.).

USSR Patent No. 874089 (E. I. Vail et al.) discloses a process for dehydration of flotation products such as coal slurry by extraction of water with ethylene glycol n-butyl ether. The ratio of ethylene glycol n-butyl ether to water is 0.5:1-4:1 and the temperature at which the extraction takes place is from 7-49° C.

Known liquid-liquid extraction processes used to recover and concentrate organic compounds and proteins tend to be expensive, because of having a large number of steps, unfavorable partitioning (uneconomically low distribution ratios), poor selectivity for the desired solute, or poor efficiency for recovery of the solvents used. An improved method that allows the concentration of valuable proteins dissolved in aqueous solutions without significant deactivation of the proteins has now been discovered. This method uses glycol ethers having inverse solubility with respect to water in known liquid-liquid extraction equipment.

The present invention concerns a method for extracting water from an aqueous solution of a protein comprising the steps of: (a) intermixing the aqueous solution of the protein with a sufficient quantity of at least one glycol ether at a temperature at least 30 centigrade degrees above the lower critical solution temperature (LCST), preferably at least 20 centigrade degrees above the LCST, and most preferably at least 10 degrees above the LCST, to form a suspension comprising a concentrated aqueous protein phase and a liquid organic phase comprising said at least one glycol ether and at least 10 percent water extracted from the aqueous solution of the protein, wherein the glycol ether has an inverse solubility in water and does not significantly deactivate or degrade the protein, and (b) separating the concentrated protein phase formed in step (a) from at least a portion of the liquid organic phase.

The method of the present invention is useful for concentrating aqueous solutions of proteins by extracting water therefrom. The solutions of proteins that can be conveniently concentrated according to the method of the present invention include aqueous solutions of temperature-sensitive proteins produced via a fermentation which are likely to decompose or react when heated to temperatures greater than 50° C.

The method of the present invention is particularly useful for concentrating enzymes and therapeutic proteins obtained by a fermentation process in dilute aqueous form. Aqueous solutions of all known classes of enzymes (that is, oxidoreductases, transferases, hydrolases, lyases, isomerases and ligases) are suitably concentrated according to the method of the present invention. The present method is particularly suitable from extracting water from aqueous solution of hydrolases such as, for example, amylase.

Any glycol ether or glycol ether blend that exhibits inverse solubility in water, with the proviso that the solubility of the glycol ether in water is significantly less than the solubility of water in the glycol ether, and the glycol ether does not significantly deactivate or degrade the protein is suitable for use in the method of the present invention. These glycol ethers are well known in the art and various methods for their preparation are described in the literature and practiced commercially. Some of the benefits of using glycol ethers in the present invention are their low aquatic and mammalian toxicity, their biodegradability, and their commercial availability.

Glycol ethers useful in the method of the present invention have the formula

R'—(OCHR"CHR")$_n$—O—R''' wherein R' is an alkyl group of 1 to 8 carbon atoms; R" is, independently in each occurrence, hydrogen, methyl or ethyl; R''' is hydrogen, an alkyl group having from 1 to 4 carbon atoms, a propionyl or an acetyl group and n is an integer between 1 and 4. Non-limiting examples of suitable glycol ethers are tripropylene glycol ethyl ether, propylene glycol isopropyl ether, dipropylene glycol isopropyl ether, tripropylene glycol isopropyl ether, propylene glycol n-propyl ether, dipropylene glycol n-propyl ether, propylene glycol t-butyl ether, dipropylene glycol t-butyl ether, tripropylene glycol t-butyl ether, propylene glycol n-butyl ether, dipropylene glycol n-butyl ether, tripropylene glycol n-butyl ether, propylene glycol n-pentyl ether, propylene glycol n-hexyl ether, butylene glycol methyl ether, dibutylene glycol methyl ether, butylene glycol ethyl ether and dibutylene glycol ethyl ether, ethylene glycol n-butyl ether, ethylene glycol n-pentyl ether, ethylene glycol n-hexyl ether, ethylene glycol n-heptyl ether, ethylene glycol 2-ethylhexyl ether, diethylene glycol n-pentyl ether, diethylene glycol n-hexyl ether, diethylene glycol n-heptyl ether, triethylene glycol n-hexyl ether, ethylene glycol n-butyl ether acetate, propylene glycol isobutyl ether, dipropylene glycol isobutyl ether, tripropylene glycol isobutyl ether, ethylene glycol t-butyl ether, ethylene glycol isobutyl ether, ethylene glycol isobutyl ether acetate, and diethylene glycol n-butyl ether acetate, and blends thereof. These glycol ethers are well known in the art and various methods for their preparation are described in the literature and practiced commercially. It is well known to a person of ordinary skill in the art that some of the listed glycol ethers will be suitable for use in the present invention at a particular temperature but not at all contemplated temperatures.

These glycol ethers exhibit inverse solubility in water such that the solubility in water at 100° C. is at least 1 weight percent less than the solubility in water at −5° C. This inverse solubility behavior can be attributed to temperature-sensitive hydrogen bonding. It is known that many glycol ethers exhibit a lower critical solution temperature (LCST) below which they are completely miscible with water. At temperatures below the LCST, the glycol ether is able to form hydrogen bonds with water and this attractive interaction leads to complete miscibility. At temperatures above the LCST, hydrogen bonding is disrupted by increasing thermal energy and hydrophobic interactions between the glycol ether and water begin to dominate. This results in partial miscibility and a decrease in the solubility of the glycol ether in water with increasing temperature (termed inverse solubility). Depending on the particular glycol ether, the LCST can be as low as −10° C. or as high as 100° C. Preferably, the glycol ether useful in the method of the present invention should be capable of transporting at least 10 percent water into the organic layer and should not significantly deactivate or degrade the protein.

In addition to glycol ethers that exhibit inverse solubility in water, water miscible glycol ethers that are completely miscible in water in all proportions may be used in the invention if they are blended with a glycol ether that exhibits inverse solubility behavior such that the resulting glycol ether blend exhibits inverse solubility behavior. Propylene glycol methyl ether is an example of such a water miscible glycol ether. The glycol ethers used in the invention may also be blended with other types of organic solvents including water miscible organic solvents and hydrophobic organic solvents provided that the resulting blend exhibits inverse solubility behavior in water.

The method of the present invention involves the steps of: (a) intermixing the aqueous solution of the protein with a sufficient quantity of at least one glycol ether at a temperature not more than 30 centigrade degrees above the lower critical solution temperature (LCST), preferably not more than 20 centigrade degrees above the LCST, and most preferably not more than 15 degrees above the LCST, to form a suspension comprising a concentrated aqueous protein phase and a liquid organic phase comprising said at least one glycol ether and water extracted from the aqueous solution of the protein; and (b) separating the concentrated aqueous protein phase formed in step (a) from the liquid organic phase.

Thus, according to the present invention, water is extracted from an aqueous stream containing protein by a liquid-liquid extraction process using a glycol ether that does not significantly degrade or inactivate the protein and exhibits inverse solubility with respect to water. The separation of the concentrated aqueous protein phase from the liquid organic phase in step (b) is conveniently conducted in a phase separator vessel via decantation or centrifugation.

If desired, the glycol ether used in the method of the present invention can be recovered from the liquid organic phase and recycled into the method. It may also be desirable to remove dissolved glycol ether from the concentrated aqueous protein phase in order to meet protein specifications. The recovery of glycol ether can be done by any known solvent recovery method such as distillation at low pressure and temperature or membrane-based methods. After separation in step (b), the amount of dissolved glycol ether in the concentrated aqueous protein phase may be reduced by heating the phase to a higher temperature to reduce the saturation amount of glycol ether, provided that heating does not significantly deactivate the protein.

In cases where dissolved glycol ether present in the concentrated aqueous protein phase has high relative volatility with respect to water, the glycol ether may conveniently be recovered for recycle back into the process using steam stripping as the recovery method, unless the required temperature results in significant deactivation of the protein.

In cases where steam stripping the glycol ether is not feasible, the addition of a hydrophobic organic solvent to the liquid organic phase may provide an efficient method for recovering the glycol ether for recycle back to the process via extraction of the glycol ether into the hydrophobic organic solvent. The use of such a hydrophobic organic solvent must not result in significant deactivation of the desired protein.

The temperature at which the intermixing of the glycol ether with the aqueous stream in step (a) of the method of the present invention is conveniently carried out at a temperature between about −5° C. and 100° C., preferably between about −5° C. and 70° C. The temperature should not be more than 30° C., preferably no more than 20° C., above the lower critical solution temperature (LCST). The temperature used is dependent upon the particular glycol ether used and the properties of the protein.

The temperature at which the glycol ether is recovered from the liquid organic phase is higher than the temperature used in step (a). In general, this temperature shall be between about 10° C. and about 100° C. and will also depend on the particular glycol ether used and the properties of the protein.

The method of the present invention is advantageously carried out at atmospheric pressure, although higher and lower pressures may be used in certain cases.

A person of an ordinary skill in the art may readily select the amount of glycol ether that may be used. Generally speaking sufficient glycol ether must be used to remove a desired amount of water from aqueous solution of the protein. This can be readily determined by experimentation. Those skilled in the art will also recognize that when used in a large excess below or near the LCST, the glycol ether will dissolve most of the water and may cause the precipitation of the protein from the aqueous solutions.

Also, a person of an ordinary skill in the art may readily select the amount of the hydrophobic solvent that may be used in the invention. In general, the hydrophobic organic solvent should be used in sufficient amount to extract dissolved glycol ether from the liquid organic phase. This also can be readily determined by experimentation.

As used in the present invention, the term "without significantly deactivating the protein" means that not more than about 80 percent of the protein is deactivated.

As used in the present invention, the term "the solubility of the glycol ether in water is significantly less than the solubility of water in the glycol ether" means that the solubility of glycol ether in water is at most 90 percent of the solubility of water in the glycol ether at a given temperature.

The method of the present invention can be carried out in a batch operation or continuously, and may be conducted in any conventional single stage or multiple stage liquid-liquid extraction equipment.

The extraction equipment useful in the present invention is well known in the art and includes a mixing vessel for intermixing the glycol ether stream with the aqueous solution of the protein and phase separation vessel where the liquid organic phase and the concentrated aqueous protein phase are separated via decantation or centrifugation. Various configurations of mixing and phase separation vessels useful in the method of the present invention are well known and commercially available from different sources. The extraction equipment can additionally involve additional equipment for recovery and recycling of the glycol ether from both, the liquid organic phase containing extracted water and glycol ether, and the concentrated aqueous phase containing the protein. The extraction equipment can also involve distillation equipment for recovery of a hydrophobic organic solvent, if used. The glycol ether can be recovered in a known manner, such as, for example by distillation under vacuum, evaporation, or extraction with a hydrophobic solvent for recycle into the mixing vessel.

Typically, the aqueous solution of the protein and a glycol ether are fed into a mixing vessel at a temperature between about −5° C. and about 100° C. where they are well intermixed. The suspension formed in the extraction column is then fed into a phase separation vessel where two phases are formed, that is, the liquid organic phase, containing all or a predominant portion of the glycol ether, and the concentrated aqueous protein phase. These two phases are then separated either by decantation or centrifugation.

In some embodiments a significant amount of glycol ether may be allowed to remain with the aqueous protein phase. Such glycol ether may comprise, for example, from about 1 to about 30 percent by weight of the aqueous protein phase. Allowing a portion of the glycol ether to remain with the aqueous protein phase may be desirable for applications such as cleaning and stain removal, where the glycol ether may positively contribute to the effectiveness of the concentrated aqueous protein phase. Thus, it may be desirable in some embodiments to effect less than a complete separation of the phases via the decantation or centrifugation. In other embodiments it may be desirable to separate substantially all of the liquid organic phase from the aqueous protein phase. By "substantially" is meant herein a separation wherein less than about 1 percent by weight of the aqueous protein phase is the liquid organic.

If desired, additional equipment can be used in the method of the present invention such as one or more vessels for recovery of the glycol ether from the liquid organic phase, one or more vessels for recovery of the hydrophobic solvent, when used, and one or more vessels for recovery of the residual glycol from the concentrated aqueous protein phase. Such additional equipment and its use in liquid-liquid extraction methods are well known in the art. A person of an ordinary skill in the art would use such additional equipment or combination thereof in the method of the present invention in a manner known for use of such equipment in conventional liquid-liquid extraction methods. The use of such additional equipment or combination thereof will depend on many factors, such as, for example, the nature of the protein, the nature of the glycol ether used, the use of the hydrophobic organic solvent, and the expenses associated with the use of glycol ether and/or hydrophobic solvent, that is desired extraction method economics. When desired, the recovered glycol ether can be recycled to the mixing vessel.

The residual glycol ether present in the concentrated aqueous protein phase can also be recovered in a known manner, such as, for example by distillation under vacuum, evaporation or extraction with a hydrophobic organic solvent and combined with the glycol ether recovered from the liquid organic phase for recycle into the mixing vessel.

In a method of the present invention wherein a hydrophobic organic solvent is used to recover the glycol ether, the liquid organic phase comprising the glycol ether and the hydrophobic organic solvent exiting from the separation vessel is fed into the distillation equipment wherein the glycol ether is separated from the hydrophobic organic solvent. The separated glycol ether is then recycled back into the mixing vessel. The hydrophobic organic solvent recovered from the liquid organic phase can be recycled into the method.

All parts, percentages and ratios herein are by weight unless otherwise indicated.

The invention will be further clarified by a consideration of the following examples which are intended to be purely exemplary of the present invention.

The following glycol ethers are employed in the examples:
Propylene glycol n-propyl ether (PnP);
Dipropylene glycol n-propyl ether (DPnP);
Dipropylene glycol dimethyl ether (DMM);
Tripropylene glycol n-propyl ether (TPnP); and
Ethylene glycol n-butyl ether (EB).

EXAMPLES 1-10

A frozen aqueous enzyme concentrate of pH 4.6, containing approximately 1.66 percent by weight α-amylase as well as sand and other particulates, is used to prepare a stock enzyme solution. The vial containing the frozen enzyme concentrate is placed in a water bath at room temperature for one-hour to thaw out the sample. Once the sample is thawed, a magnetic stir bar is placed in the vial and the sample is stirred on a stir plate for approximately 10 minutes. At this time, the sample is light brown in color and appears homogeneous. A 0.7229 g sample of the concentrate is then quickly pipetted into a tared 2-oz. glass jar. The sample is then diluted to 345.3 parts-per-million (ppm) by adding 34.0346 g of a pH 4.0 potassium biphthalate buffer. The jar is then sealed and shaken vigorously until the stock solution is well mixed. Approximately 10 g of the pH 4.0 stock enzyme solution and 10 g glycol ether indicated in Table 1 below is added to a 50-mL calibrated centrifuge vial. The vial is then shaken vigorously for 5 minutes and placed in a Brinkmann Lauda RM6 Heating/Cooling Circulator. The temperature is initially set to match the expected LCST for the pure water-glycol ether system (about 32° C. in the case of PnP) and incrementally increased by 1° C. until a two phase system is present at the temperature indicated in Table 1 below. During this time, the vial is sporadically shaken and then allowed time to equilibrate at the set temperature. Once the two-phases are defined by a sharp interface, two samples are taken from each layer using disposable pipettes, one for liquid chromatography (LC) analysis and one for gas chromatography (GC) analysis. The organic layer is pipetted out of the vial before sampling the aqueous layer. Each of the four samples weigh approximately 1.0 g. The samples are placed in tared 4-dram vials and sealed with polyseal caps. LC samples are diluted with water in a 10:1 weight ratio (water to sample), and GC samples are diluted with tetrahydrofuran (THF) in a 5:1 weight ratio (THF to sample). The sample vials are shaken, and then portions of these dilute solutions are transferred into autosampler LC/GC vials for analysis. An enzyme activity test described by D. Plummer in Chapter 10, sections 10.1 and 10.8 of *An Introduction to Practical Biochemistry* (McGraw-Hill, 1971) is performed using the remainder of the dilute solutions made for the LC analysis. This test detects the sugar maltose produced when the alpha-amylase enzyme hydrolyzes the alpha-1→4 links of a starch sample. A spectrophotometer is used to measure the absorbance of the resulting maltose solution at 540 nm. Conditions for the HPLC, GC, and enzyme activity analyses follow. The experimental results obtained are shown in Table 1.

HPLC Analyses

Enzyme concentrations were established by high pressure liquid chromatography (HPLC) using an Agilent 1100 Series Liquid Chromatograph equipped with an ultraviolet (UV) detector set at 280 nm, and a Dell Ultra Scan P1110 ChemStation. The instrument was fitted with a PLRP-S 5 micron, 100 A, 250×4.6 mm reversed phase column from Polymer Labs. The mobile phase was composed of (A) 0.025 M ammonium acetate (adjusted to pH 9 with NH$_4$OH) and 10 percent acetonitrile; and (B) 0.025 M ammonium acetate (adjusted to pH 9 with NH$_4$OH) and 70 percent acetonitrile. The analysis used a flow rate of 1 mL/min and a gradient of 100 percent (A) to 35 percent (A) in 40 minutes with a 3 minute hold. Injection size was 25 microliters. Samples were prepared by diluting 1.00 g of the aqueous or solvent test solution with 10.00 g HPLC grade water. Calibration standards contained between 10 and 1000 ppm alpha-amylase GC Analyses Water and solvent concentrations were established by capillary gas chromatography. A Hewlett-Packard 6890 gas chromatograph equipped with capillary inlets, thermal conductivity detectors (TCD), HP-7683 autoinjectors, and a ChemStation was used for these analyses. Samples and calibration standards were diluted 5:1 with tetrahydrofuran (THF), which was used as the diluent, internal standard, and reference solvent. Calibrations were made using a 50 weight percent solvent in water solution after establishing the linearity range for the analyses. Data were recorded as the average of multiple injections.

Enzyme Activity Tests

Preparation of Test Reagents. A phosphate buffer (0.1 M, pH 6.86) was prepared using a commercially available, ready-to-dilute, phosphate buffer salt concentrate. A 1 percent NaCl solution was prepared by dissolving the appropriate amount of NaCl in water. A buffered starch substrate was made using the prepared phosphate buffer (0.5 percent starch in phosphate buffer). Soluble starch (5 g) and a stir bar were placed in a tared beaker which was then placed on a stirring plate. Phosphate buffer (50 mL) was added, and the resulting mixture stirred until a smooth paste was obtained. The paste was added to 500 mL of boiling phosphate buffer and allowed to boil for about one minute. The solution was then cooled to room temperature and diluted to 1 L with the phosphate buffer. A dinitrosalycilate reagent required for the test was prepared as follows: Sodium potassium tartrate (150 g) was dissolved in water (250 mL) in a volumetric flask. The 3,5-dinitrosalicylic acid was placed in a tared along with 2N sodium hydroxide (100 mL) and a magnetic stir bar. The beaker was then placed on a stirred hot-plate and the mixture heated to about 60° C. The mixture was allowed time to heat and stir until a solution formed. While still hot, the contents of the beaker were placed in a 500-mL volumetric flask that already contained the sodium potassium tartrate solution. The reagent mixture was then diluted to 500 mL.

Test Procedure. Tests were conducted in a series of 50 mL vials, one of which was labeled as the blank. To each of the vials was added 0.5 percent starch solution (12.5 mL), 0.1 M phosphate buffer (5 mL), and 1 percent NaCl solution (2.5 mL). Water (2.5 mL) was added to the vial labeled as the blank. A sample of a given aqueous or solvent test solution (2.5 mL) was added to another vial which was then labeled appropriately. This last step was repeated with the remaining test samples, each time using a different vial. The vials were capped and placed in a 37° C. water bath for 20 minutes. The vials were removed from the bath and the enzymatic reaction quenched by the addition of 2N NaOH (2.5 mL) to all of the vials. The dinitrosalicylate reagent (2.5 mL) was added to each of the vials which were then capped and heated for exactly 5 minutes in a boiling water bath. The vials were allowed to cool to room temperature before transferring the contents to cuvettes. A Hach DR/2010 Spectrophotometer was used to measure the absorbance of each solution at a wavelength of 540 nm. The blank was used to zero the instrument. The test was interpreted to indicate a reduction of activity if the measured absorbance value was lower than the absorbance value measured for a starch sample treated with a stock solution of alpha-amylase. The activity was considered to be fully retained if the absorbance value was the same or higher. The results were reduced to Yes (activity was retained) and No (a significant reduction of activity had occurred).

TABLE 1

| | | Experimental Conditions* | | | Aqueous Layer (wt %) | | | Organic Layer (wt %) | | | Activity Test |
|---|---|---|---|---|---|---|---|---|---|---|---|
| | | | pH of | | | | | | | | |
| Ex. | Glycol Ether | Amylase (ppm) | Enzyme Solution | Temp. (° C.) | Glycol Ether | Water | Amylase (ppm) | Glycol Ether | Water | Amylase (ppm) | (Absorbance)[#] Aqueous Layer |
| 1 | PnP | 345.3 | 4 | 38 | 26.26 | 73.68 | 675 | 59.78 | 40.22 | 0.0 | 3.55 |
| 2 | PnP | 329.4 | 4 | 34 | 29.5 | 70.43 | 723 | 57.16 | 42.84 | 0.0 | 3.44 |
| 3 | PnP | 334.2 | 2 | 32 | 23.09 | 76.91 | 0.0 | 62.47 | 37.53 | 10.4 | 0.28[##] |
| 4 | DPnP | 335.7 | 7 | 25 | 15.96 | 84.00 | 374 | 78.5 | 21.50 | 0.0 | 3.63 |
| 5 | DPnP | 345.3 | 4 | 17 | 30.99 | 68.97 | 400 | 62.89 | 37.11 | 0.0 | 3.72 |
| 6 | EB** | 235.4 | 4 | 70 | 15.57 | 84.4 | 262 | 48.86 | 51.13 | 11.8 | 3.36 |
| C-1*** | DMM | 334.6 | 5 | 10 | 42.51 | 57.47 | 182 | 94.93 | 5.07 | 0.0 | 3.40 |
| C-2*** | DMM | 335.9 | 4 | 10 | 43.96 | 56.02 | 187 | 94.19 | 5.81 | 0.0 | 3.46 |
| C-3*** | TPnP | 334.6 | 5 | 10 | 25.91 | 74.06 | 306 | 77.95 | 22.05 | 0.0 | 3.32 |
| C-4*** | TPnP | 335.9 | 4 | 10 | 31.08 | 68.89 | 338 | 76.92 | 25.86 | 0.0 | 3.46 |

*The experimental charge is a 50/50 weight ratio of buffered amylase solution to Glycol Ether
**The experimental charge is a 60/40 ratio of buffered amylase solution to Glycol Ether increasing the aqueous layer's size for sampling
***not an Example of the present invention
[#]Maximum absorbance seen with a standard having a concentration of approximately 30 ppm α-amylase is 3.50 ± 0.25
[##]Observed formation of white precipitate at the interface In Example 1 that is conducted at temperature of 38° C., the LC analysis shows that the a-amylase concentration in the aqueous phase had essentially doubled to 675 ppm and that no enzyme was present in the organic phase. The GC analysis showed that the organic layer contained 40.2 weight of water. The results of the enzyme activity test showed that the enzyme in the aqueous layer remained active after contacting particular glycol ether. For this particular enzyme, pH is a critical factor since the enzyme becomes insoluble in water at pH 2.0. In Example 2 conducted at temperature of 34° C., very similar results were obtained. Examples 4, 5, and 6 conducted with DPnP and EB demonstrate that these glycol ethers also extract water from the enzyme solution and concentrate the enzyme without loss of activity. In Comparative Examples C-3 and C-4 conducted with TPnP, the transfer of water into the organic phase was balanced by a similar amount of glycol ether transferring into the aqueous phase, so that the net result was little or no change in the concentration of protein in the aqueous phase. In Comparative Examples C-1 and C-2 conducted with DMM, DMM partitioned preferentially into the water phase making it larger and diluting the enzyme.

The invention claimed is:

1. A method for extracting water from an aqueous solution of a protein, the method comprising:
   intermixing the aqueous solution of the protein with a sufficient quantity of at least one glycol ether at a temperature between 10 centigrade degrees above the lower critical solution temperature (LCST) and 30 centigrade degrees above the LCST, to form a suspension comprising a concentrated aqueous protein phase and a liquid organic phase comprising said at least one glycol ether and at least 10 percent water extracted from the aqueous solution of the protein,
   separating the concentrated aqueous protein phase from the liquid organic phase and recovering a separated concentrated aqueous protein phase and a separated liquid organic phase wherein the glycol ether has an inverse solubility in water, and the solubility of the glycol ether in water is at most 90% of the solubility of water in the glycol ether at the temperature at which the intermixing is performed, and wherein the protein in the separated concentrated aqueous protein phase is not significantly deactivated.

2. The method according to claim 1, wherein the glycol ether has the formula:

$R'—(OCHR''CHR'')_n—O—R'''$, wherein R' is an alkyl group of 1 to 8 carbon atoms, wherein R'' is hydrogen, methyl or ethyl, wherein R''' is selected from the group consisting of hydrogen, an alkyl group having from 1 to 4 carbon atoms, a propionyl group, and an acetyl group and wherein n is an integer between 1 and 4.

3. The method according to claim 1, wherein the intermixing of the glycol ether with the aqueous solution of the protein is conducted at a temperature between about −5° C. to about 70° C.

4. The method according to claim 1, wherein the separated concentrated aqueous protein phase comprises glycol ether in an amount from about 1 to about 30 percent by weight.

5. The method according to claim 1, wherein substantially all of the liquid organic phase is separated from the concentrated aqueous protein phase.

6. The method according to claim 1, the method further comprising heating the separated and recovered liquid organic phase to a temperature that is higher than the temperature at which the intermixing is performed, to form a suspension comprising an aqueous phase and a glycol ether phase; and separating the glycol ether phase from the aqueous phase.

7. The method according to claim 6, wherein the separated and recovered liquid organic phase is heated at a temperature of from about 40° C. to about 100° C. between about 40° C. and about 100° C.

8. The method according to claim 1, wherein the concentrated aqueous protein phase is contacted with a hydrophobic organic solvent.

9. The method according to claim 6, wherein the aqueous phase is contacted with a hydrophobic organic solvent.

10. The method according to claim 1, wherein the protein is an enzyme or a therapeutic protein.

11. The method according to claim 2, wherein the glycol ether is selected from the group consisting of tripropylene glycol ethyl ether, propylene glycol isopropyl ether, dipropylene glycol isopropyl ether, dipropylene glycol dimethyl ether, tripropylene glycol n-propyl ether, tripropylene glycol isopropyl ether, propylene glycol n-propyl ether, dipropylene glycol n-propyl ether, propylene glycol t-butyl ether, dipropylene glycol t-butyl ether, tripropylene glycol t-butyl ether, propylene glycol n-butyl ether, dipropylene glycol n-butyl ether, tripropylene glycol n-butyl ether, propylene glycol n-pentyl ether, propylene glycol n-hexyl ether, butylene glycol methyl ether, dibutylene glycol methyl ether, butylene glycol ethyl ether dibutylene glycol ethyl ether, ethylene glycol n-butyl ether, ethylene glycol n-pentyl ether, ethylene glycol n-hexyl ether, ethylene glycol n-heptyl ether, ethylene glycol 2-ethylhexyl ether, diethylene glycol n-pentyl ether, diethylene glycol n-hexyl ether, diethylene glycol n-heptyl ether, triethylene glycol n-hexyl ether, ethylene glycol n-butyl ether acetate, propylene glycol isobutyl ether, dipropylene glycol isobutyl ether, tripropylene glycol isobutyl ether, ethylene glycol t-butyl ether, ethylene glycol isobutyl ether, ethylene glycol isobutyl ether acetate, and diethylene glycol n-butyl ether acetate, and blends thereof.

12. The method according to claim 11, wherein the glycol ether is selected from the group consisting of propylene glycol n-propyl ether, dipropylene glycol n-propyl ether, dipropylene glycol dimethyl ether, tripropylene glycol n-propyl ether, and ethylene glycol n-butyl ether.

13. The method according to claim 1, wherein the concentrated aqueous protein phase is separated from the liquid organic phase by centrifugation.

14. The method according to claim 1, the method further comprising recovering the glycol ether.

15. The method according to claim 1, wherein the protein is a temperature-sensitive protein.

\* \* \* \* \*